United States Patent
Jean-Charles et al.

(10) Patent No.: US 10,500,368 B2
(45) Date of Patent: Dec. 10, 2019

(54) DENTAL SYRINGE

(71) Applicants: Germain Jean-Charles, Pittsford, NY (US); Ajay Ramesh Kashi, Rochester, NY (US)

(72) Inventors: Germain Jean-Charles, Pittsford, NY (US); Ajay Ramesh Kashi, Rochester, NY (US)

(*) Notice: Subject to any disclaimer, the term of this patent is extended or adjusted under 35 U.S.C. 154(b) by 0 days.

(21) Appl. No.: 15/422,590

(22) Filed: Feb. 2, 2017

(65) Prior Publication Data

US 2018/0021541 A1 Jan. 25, 2018

Related U.S. Application Data

(60) Provisional application No. 62/365,009, filed on Jul. 21, 2016.

(51) Int. Cl.
| | |
|---|---|
| *A61M 19/00* | (2006.01) |
| *A61M 5/24* | (2006.01) |
| *A61M 5/31* | (2006.01) |
| *A61M 5/315* | (2006.01) |
| *A61M 5/50* | (2006.01) |

(52) U.S. Cl.
CPC ............ *A61M 19/00* (2013.01); *A61M 5/24* (2013.01); *A61M 5/2466* (2013.01); *A61M 5/3137* (2013.01); *A61M 5/31515* (2013.01); *A61M 2005/2414* (2013.01); *A61M 2005/2485* (2013.01); *A61M 2005/3139* (2013.01); *A61M 2005/5073* (2013.01); *A61M 2210/0625* (2013.01); *A61M 2210/0631* (2013.01)

(58) Field of Classification Search
CPC ............ A61M 5/2466; A61M 5/3137; A61M 5/31501; A61M 2005/2474; A61M 2005/2485; A61M 2005/3139
See application file for complete search history.

(56) References Cited

U.S. PATENT DOCUMENTS

| | | | | |
|---|---|---|---|---|
| 5,112,307 | A * | 5/1992 | Haber | A61M 5/24 604/110 |
| 5,562,623 | A * | 10/1996 | Shonfeld | A61M 5/5013 604/110 |
| 5,607,399 | A * | 3/1997 | Grimard | A61M 5/315 604/220 |
| 5,738,655 | A * | 4/1998 | Vallelunga | A61M 5/5066 604/110 |
| 7,320,680 | B2 * | 1/2008 | Shue | A61M 5/5066 604/110 |

(Continued)

OTHER PUBLICATIONS

Definition of retaining (Dictionary.com on Mar. 9, 2018).*

*Primary Examiner* — Laura A Bouchelle
*Assistant Examiner* — Dung T Ulsh
(74) *Attorney, Agent, or Firm* — Sonya C. Harris; Invention Services

(57) ABSTRACT

A device or arrangement for a carpule for a dental syringe permits the harpoon on the distal end of the plunger rod to engage the rubber or rubber-like plug or piston of the carpule, but blocks the piston from being pulled out the open proximal end of the tubular glass body of the carpule. A preferred version has an apertured cap that fits onto the proximal end of the carpule, a retaining neck ring that fits onto the penetrable seal at the proximal end of the carpule, and a bar connecting them. The bar also serves as a grip to assist in handling the carpule.

3 Claims, 2 Drawing Sheets

(56) References Cited

U.S. PATENT DOCUMENTS

| | | | |
|---|---|---|---|
| 9,055,992 B2* | 6/2015 | Larson | A61C 19/08 |
| 9,345,833 B1* | 5/2016 | Alabdulwahhab | A61M 5/2466 |
| 2012/0310160 A1* | 12/2012 | Javid | A61M 5/322 |
| | | | 604/110 |
| 2016/0175532 A1* | 6/2016 | Gutierrez | A61M 5/3137 |
| | | | 604/194 |
| 2017/0165432 A1* | 6/2017 | Russo | A61M 5/31511 |
| 2017/0281872 A1* | 10/2017 | Guthart | A61M 5/31501 |
| 2017/0290987 A1* | 10/2017 | Mandaroux | A61M 5/31513 |
| 2017/0312452 A1* | 11/2017 | Sawyer | A61M 5/3245 |
| 2017/0361023 A1* | 12/2017 | Anderson | A61M 5/31511 |
| 2018/0021541 A1* | 1/2018 | Jean-Charles | A61M 19/00 |

* cited by examiner

DENTAL SYRINGE

This application claims priority under 35 U.S.C. § 119(e) of provisional application Ser. No. 62/365,009, filed Jul. 21, 2016, the disclosure of which is incorporated by reference herein.

BACKGROUND OF THE INVENTION

This invention is directed to a dental syringe and carpule, of the type used to administer a local anesthetic or other medication to a dental patient. The carpule, containing anesthetic, for example, is inserted into the barrel of the syringe, and a needle on the distal end of the syringe pierces a puncturable seal on the carpule. The plunger of the syringe contacts a rubber or rubber-like piston that can be pushed forward to eject the anesthetic solution into the patient's gum or jaw.

In most current syringes, the plunger has a barbed member, i.e., a "harpoon" at its distal end and the harpoon pierces and engages the piston. This permits the dental practitioner to pull back on the plunger to withdraw the piston proximally, which causes the syringe to aspirate, i.e., to draw fluids back in through the needle. In order to remove the carpule from the barrel of the syringe, the dentist pulls back on the plunger to withdraw the plunger from the carpule. However, it frequently occurs that the harpoon fails to disengage from the piston or plug, and the piston is pulled out from the proximal end of the tube of the carpule.

OBJECTS AND SUMMARY OF THE INVENTION

It is an object to improve the dental syringe so that inadvertent withdrawal of the piston is avoided.

Accordingly, the improved dental carpule of this invention incorporates a device or member at the proximal or piston end of the carpule that blocks the piston or plug from moving past the proximal open end of the carpule when the plunger is withdrawn, holding the piston in place when the harpoon is pulled out of the piston when the plunger is withdrawn proximally. Any of several techniques can be employed to keep the piston from moving proximally past the end of the carpule. Such features prevent the distal end (i.e., "harpoon") of the plunger rod from being locked into the rubber piston after injection of the anesthetic.

DETAILED DESCRIPTION

Figure 1:
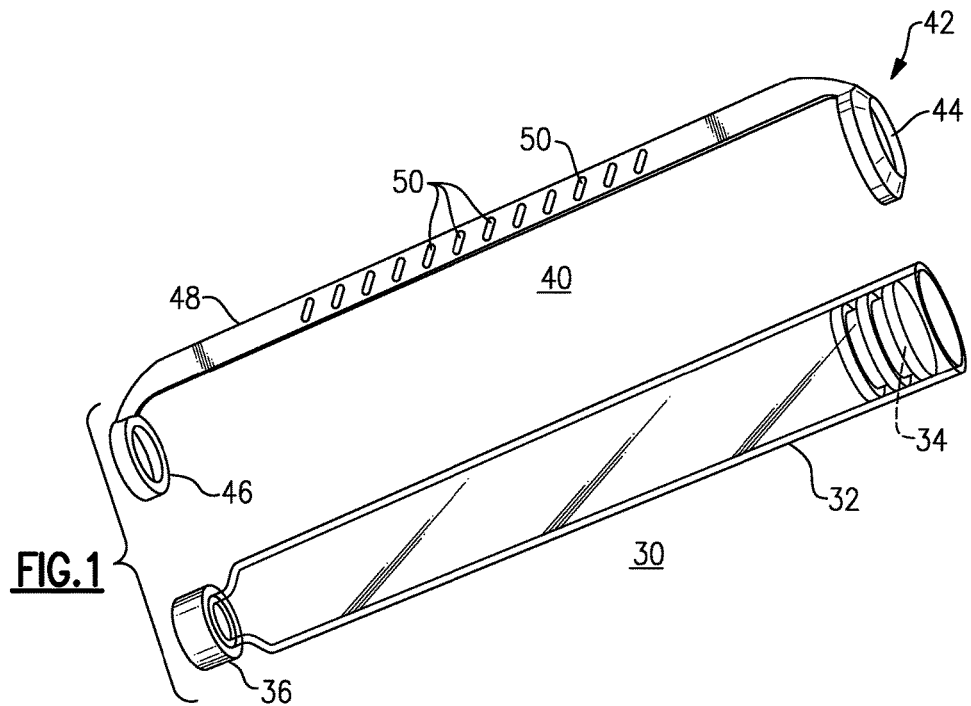
FIG. 1 is a perspective view of a carpule for dental syringe and an anti-withdrawal arrangement according to one embodiment of this invention.
Figure 2:
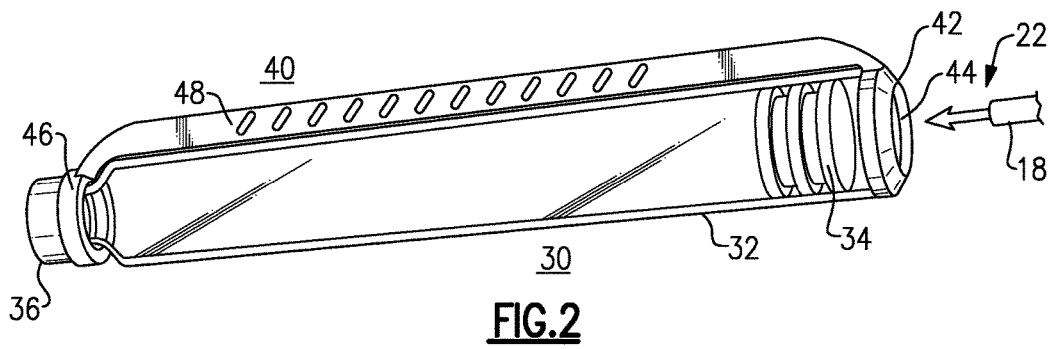
FIG. 2 is another perspective view thereof showing the anti-withdrawal arrangement installed onto the carpule.
Figure 3:
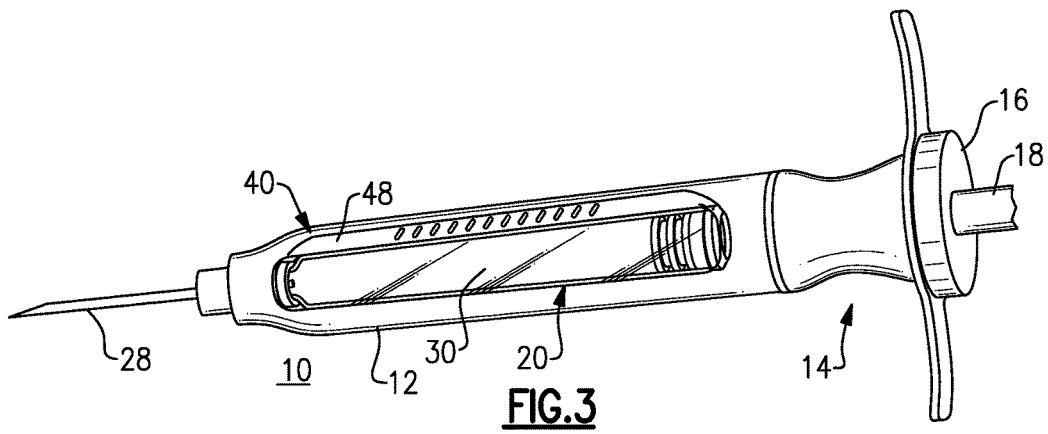
FIG. 3 is perspective view of the carpule and anti-withdrawal arrangement installed into a dental syringe of the type having a barrel portion and a plunger portion.

With reference to the above-listed Figures of Drawing, and initially to FIGS. 1 to 3, a dental syringe 10 (seen in FIG. 3) is formed of medical-grade stainless steel and is adapted to hold a replaceable cartridge ampule, or carpule 30. The carpule fits into the barrel portion 12 of the syringe, after which the plunger portion 14 of the syringe is attached, with male threads on the barrel portion 12 fitting female threads on the plunger portion 14. The plunger portion has a plunger assembly 16 with a movable operating shaft 18, here having a thumb ring (not shown) at its proximal end. A fixed part of the plunger portion 14 has finger rests that extend radially out to the sides. The barrel portion 12 has an open window 20 formed along one side to allow the dental practitioner to observe the carpule and its contents. Here the plunger operating rod 18 is seen to have a barbed pointed end or harpoon 22 (FIG. 2) supported at the distal end of the rod 18, the harpoon 22 being the portion of the plunger that engages and pushes the rubber piston of the associated carpule.

As shown in FIGS. 1 and 2, the carpule 30 is in the form of a cylindrical glass tube 32, pre-filled with a predetermined amount of medication, which in this case is a solution of a local anesthetic. The rubber plug or piston 34 serves to seal the open end of the fresh or unused carpule 30. There is a puncturable seal 36 at the distal end, and this is pierced upon insertion of the carpule by the interior end of a double-ended needle 28. This seal 36 is shown here being encased on a metal jacket at the distal end of the carpule. During administration of the contents of the carpule, the plunger rod pushes the piston 34 distally, i.e. left in these views, until it is emptied.

An anti-withdrawal cup arrangement 40 is shown in FIG. 1 as an additional member and in FIG. 2 as installed on the carpule 30. The arrangement 40 has a disk or cup, in the form of a ring 42 at the proximal end that fits onto the proximal open end of the carpule, and this ring 42 has an axial central opening 44 that is large enough to permit the harpoon 22 to pass through, but is smaller than the diameter of the piston 34. A neck ring 46 is dimensioned to fit over the distal-end seal 36 of the carpule, and an elongated bar 48 connects the neck ring 46 with the proximal-end ring 42. In this embodiment, the bar 48 is in the form of a fin or flange with textured grip members 50 along its side, which can serve as an aid for the dental practitioner in handling the carpule. The fin or flange extends axially along the length of the carpule 30, and extends out radially from the carpule.

As shown in FIG. 3, the carpule is inserted into the barrel 12 of the syringe with the bar (or fin) projecting out through the window 20 of the syringe. With the arrangement 40 in place on the carpule 30, the carpule is positioned into the barrel of the syringe and the plunger portion of the syringe is installed behind it. The plunger rod can move forward or distally so that the harpoon 22 engages the plug or piston 34, and can urge the piston distally to discharge some of the contents of the carpule out the needle 28. When the dental practitioner withdraws the plunger, the disk or ring 42 prevents the harpoon 22 on the plunger rod from pulling the plug or piston 34 out of the open end of the glass tube, and ensures that the harpoon breaks engagement with the piston. Then the carpule 30 can be removed and discarded without the plug or any residual contents leaving or spilling from it. When the plunger rod is withdrawn, it leaves engagement with the piston 34, so the piston remains in the carpule 22. Then the carpule can be removed and the syringe 10 can be prepared for further use.

In a favorable implementation of the invention, the arrangement 40 is permanently affixed onto the carpule 30, and is not an extra piece to be attached at the dental office. However, in an alternate implementation, the arrangement 40 may be removable after use, and may be re-used on another carpule.

Figure 4:
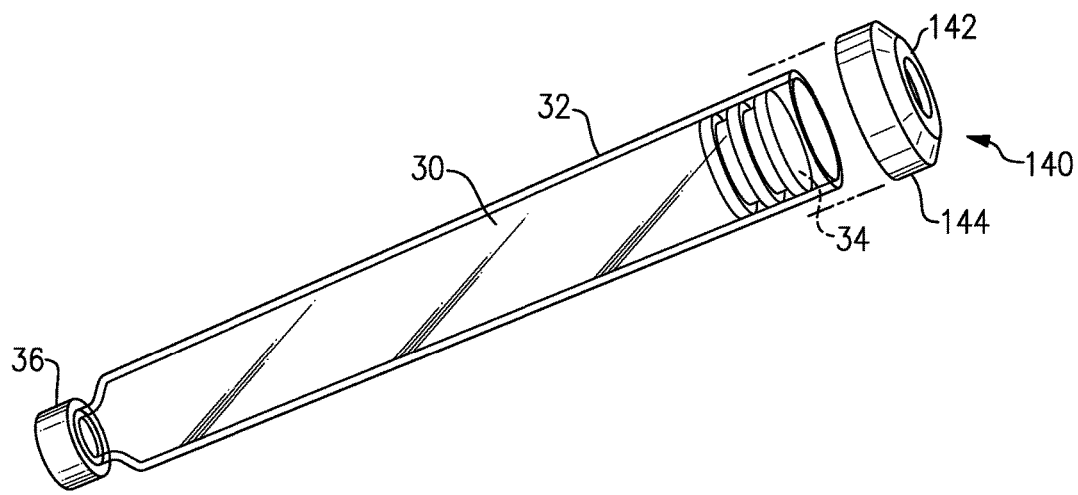
FIGS. 4 and 5 are perspective views of a carpule with an anti-withdrawal arrangement according to another embodiment of the invention.
Figure 5:
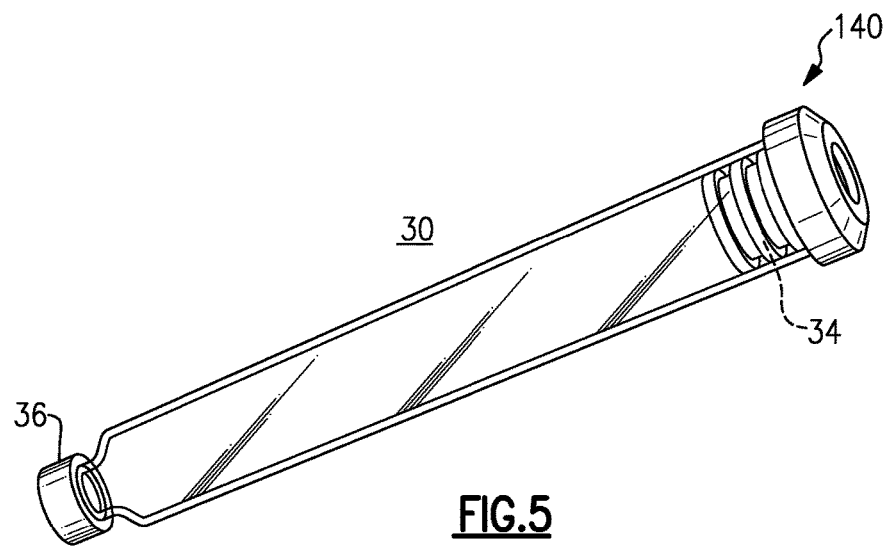

An alternative arrangement of a possible anti-withdrawal arrangement or device 140 is shown in FIGS. 4 and 5. Here, the device is in the form of a cup 142 having an end ring 144 with a central opening, and a cylindrical skirt 146 that fits tightly or snugly over the outer surface of the glass tube of the carpule at its proximal end. In this case, there is sufficient friction between the skirt 146 and the glass tube 32, so that the end ring 144 prevents the carpule piston 34 from leaving the carpule when the plunger is withdrawn, and provides enough resistance to that the harpoon pulls out of and breaks engagement with the piston. Alternatively, the cup 142 can be cemented onto the carpule.

In other possible embodiments, the carpule may comprise one-way flute structures inside the barrel or cylinder 32 of the carpule 30 adjacent the proximal end. These flutes may be glass, metal or plastic, and these may engage the piston 34 when it is at the proximal end and prevent the piston from retracting beyond the proximal end of the glass tube 32. The operating rod of the plunger may in some cases have a blunt distal surface rather than a harpoon.

While the invention is described and illustrated with selected preferred embodiments, it should be understood that these are examples only, and the main principles of the invention may be employed in many possible implementations without departing from the scope and spirit of the invention, as defined in the appended claims.

We claim:

1. A dental syringe apparatus comprising:
   a carpule, for containing a medical solution for dispensing,
      and having a length defined by a longitudinal cylindrical elongated rigid tubular body, said body having a proximal end and a distal end, and a central longitudinal opening defining a hollow interior for housing said medical solution, wherein said distal end has a first diameter and the proximal end has a second diameter,
      and wherein the first diameter of said distal end of said carpule body is smaller than the second diameter of the proximal end of said carpule; and said carpule has an exterior seal on said distal end and an interior seal on said proximal end; and
      said exterior seal is a penetrable membrane, and said interior seal is a longitudinally displacing disc dimensioned and configured to frictionally fit within and plug said proximal end; and
   a brace member comprising a substantially flat, longitudinal rectilinear rigid bar with a set of beveled first and second portions on both ends of said bar and said beveled portions having first and second rings each extending perpendicularly from said beveled first and second ends, respectively;
      wherein said first and second rings each contain a central aperture and wherein said first ring has a diameter smaller than said second ring; and said first ring is adapted and dimensioned to fit circumferentially about said exterior seal, and said second ring is adapted to fit circumferentially about said proximal end of said carpule, and wherein said exterior seal protrudes beyond said first ring, and
   a plunger assembly, for longitudinally actuating said interior seal, for dispensing said medical solution contained within said carpule and said plunger assembly having a cylindrical elongated longitudinal rigid tubular body with a proximal end and a distal end, and wherein said plunger assembly has a plunger having a handle extending perpendicularly from, and beyond said cylindrical elongated longitudinal rigid tubular body,
      and said cylindrical elongated longitudinal rigid tubular body having an elongated cylindrical aperture formed along a horizontal axis thereof, forming a window opening,
      and said plunger assembly dimensioned and configured to fit circumferentially about said brace member and said carpule, and wherein said proximal end is sized and dimensioned to receive said brace member and said carpule for insertion within said cylindrical elongated longitudinal rigid tubular body,
      and wherein said window opening has a length substantially equal to said longitudinal rectilinear bar, and dimensioned and configured such that said bar projects out through said window opening.

2. The dental syringe apparatus of claim 1, wherein the length of said brace member is substantially equal to the length of said carpule.

3. The dental syringe apparatus of claim 2, wherein said brace member has an array of friction enhancing textured grip members along the length of said longitudinal rectilinear bar.

\* \* \* \* \*